(12) United States Patent
Desembrana

(10) Patent No.: US 6,277,053 B1
(45) Date of Patent: Aug. 21, 2001

(54) CHIN AND FACE TONING STRAP

(76) Inventor: Dan Desembrana, 819 W. 148th St., Gardena, CA (US) 90247

( * ) Notice: Subject to any disclaimer, the term of this patent is extended or adjusted under 35 U.S.C. 154(b) by 0 days.

(21) Appl. No.: 09/535,032

(22) Filed: Mar. 24, 2000

(51) Int. Cl.[7] ............................................. A63B 23/025
(52) U.S. Cl. ..................................................... 482/11; 602/74
(58) Field of Search .......................... 482/10, 11; 601/15, 601/38, 134, 138; 606/204

(56) References Cited

U.S. PATENT DOCUMENTS

| | | | |
|---|---|---|---|
| 649,896 | * 5/1900 | Baughman | 602/74 |
| 1,587,558 | * 6/1926 | Sheffield | 602/74 |
| 4,666,148 | 5/1987 | Crawford | 272/95 |
| 5,336,139 | 8/1994 | Miller | 482/10 |
| 5,450,858 | * 9/1995 | Zablotsky et al. | 602/13 |
| 5,484,359 | 1/1996 | Wabafiyebazu | 482/11 |
| 5,501,646 | * 3/1996 | Miller | 482/11 |

* cited by examiner

Primary Examiner—Stephen R. Crow
(74) Attorney, Agent, or Firm—Goldstein Law Offices P.C.

(57) ABSTRACT

A chin and face toning strap including an elongated strap portion dimensioned for wrapping underneath a chin and atop head of a user. The elongated strap portion is constructed of an elastic material. The strap portion has a chin portion that is positionable under the chin of the user. The strap portion has opposed cheek portions positionable against cheeks of the user. A pair of magnets are secured within the cheek portions of the elongated strap portion.

5 Claims, 2 Drawing Sheets

CHIN AND FACE TONING STRAP

BACKGROUND OF THE INVENTION

The present invention relates to a chin and face toning strap and more particularly pertains to exercising the muscles of the face while also stimulating the flow of blood to the face.

The use of exercise devices is known in the prior art. More specifically, exercise devices heretofore devised and utilized for the purpose of exercising the facial muscles are known to consist basically of familiar, expected and obvious structural configurations, notwithstanding the myriad of designs encompassed by the crowded prior art which have been developed for the fulfillment of countless objectives and requirements.

By way of example, U.S. Pat. No. 5,484,359 to Wabafiyebazu discloses a device comprised of a plurality of straps for use in exercising the facial muscles of a user's jaw. U.S. Pat. No. 4,666,148 to Crawford and U.S. Pat. No. 5,336,139 to Miller disclose additional exercise devices.

While these devices fulfill their respective, particular objective and requirements, the aforementioned patents do not describe a chin and face toning strap for exercising the muscles of the face while also stimulating the flow of blood to the face.

In this respect, the chin and face toning strap according to the present invention substantially departs from the conventional concepts and designs of the prior art, and in doing so provides an apparatus primarily developed for the purpose of exercising the muscles of the face while also stimulating the flow of blood to the face.

Therefore, it can be appreciated that there exists a continuing need for a new and improved chin and face toning strap which can be used for exercising the muscles of the face while also stimulating the flow of blood to the face. In this regard, the present invention substantially fulfills this need.

SUMMARY OF THE INVENTION

In the view of the foregoing disadvantages inherent in the known types of exercise devices now present in the prior art, the present invention provides an improved chin and face toning strap. As such, the general purpose of the present invention, which will be described subsequently in greater detail, is to provide a new and improved chin and face toning strap which has all the advantages of the prior art and none of the disadvantages.

To attain this, the present invention essentially comprises an elongated strap portion dimensioned for wrapping underneath a chin and attaching atop a head of a user. The elongated strap portion is constructed of an elastic material. The elongated strap portion has opposed ends. The opposed ends each have a hook and loop patch disposed thereon. The hook and loop patches couple together to secure the strap portion under the chin and to the head of the user. The strap portion has a chin portion that is positionable under the chin of the user. The chin portion is defined by an enlarged section dimensioned for receiving the chin therein. The enlarged section has padding disposed therein. The strap portion has opposed cheek portions positionable against cheeks of the user. A pair of magnets are secured within the cheek portions of the elongated strap portion.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved chin and face toning strap which has all the advantages of the prior art exercise devices and none of the disadvantages.

It is another object of the present invention to provide a new and improved chin and face toning strap which may be easily and efficiently manufactured and marketed.

It is a further object of the present invention to provide a new and improved chin and face toning strap which is of durable and reliable construction.

An even further object of the present invention is to provide a new and improved chin and face toning strap which is susceptible of a low cost of manufacture with regard to both materials and labor, and which accordingly is then susceptible of low prices of sale to the consuming public, thereby making such a chin and face toning strap economically available to the buying public.

Even still another object of the present invention is to provide a new and improved chin and face toning strap for exercising the muscles of the face while also stimulating the flow of blood to the face.

Lastly, it is an object of the present invention to provide a new and improved chin and face toning strap including an elongated strap portion dimensioned for wrapping underneath a chin and atop a head of a user. The elongated strap portion is constructed of an elastic material. The strap portion has a chin portion that is positionable under the chin of the user. The strap portion has opposed cheek portions positionable against cheeks of the user. A pair of magnets are secured within the cheek portions of the elongated strap portion.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts through the various figures.

DESCRIPTION OF THE PREFERRED EMBODIMENT

Figure 1:
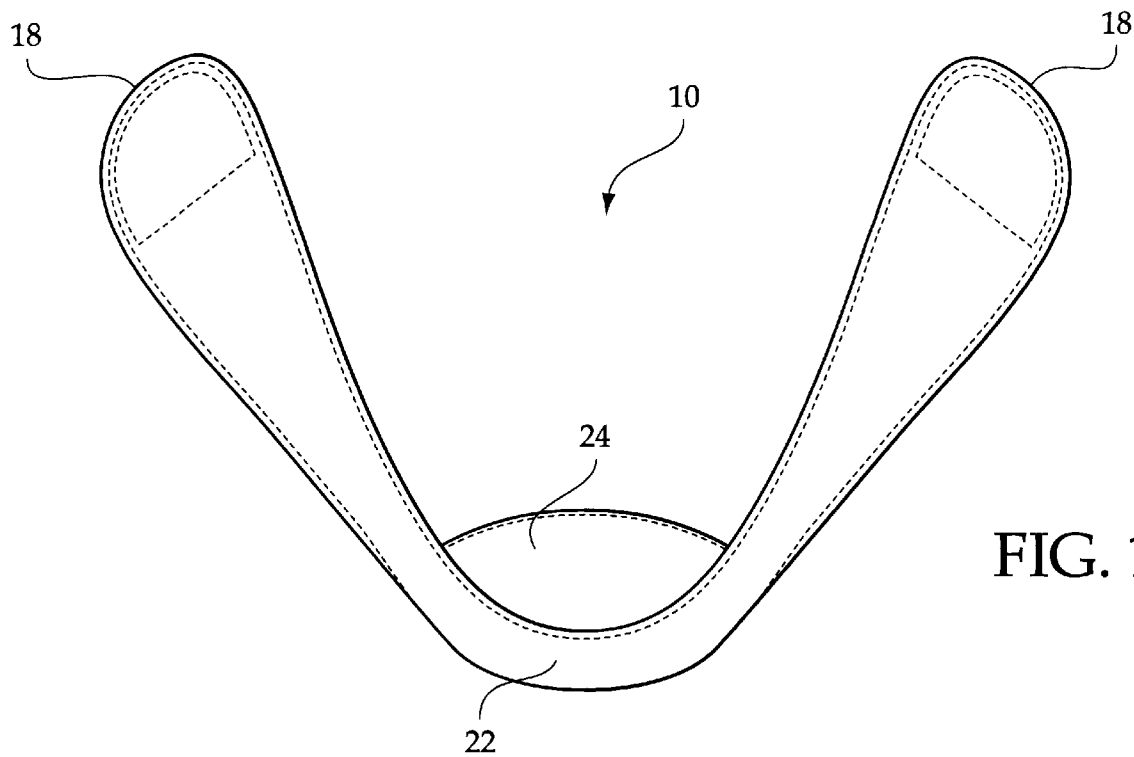
FIG. 1 is a perspective view of the preferred embodiment of the chin and face toning strap constructed in accordance with the principles of the present invention.
Figure 2:
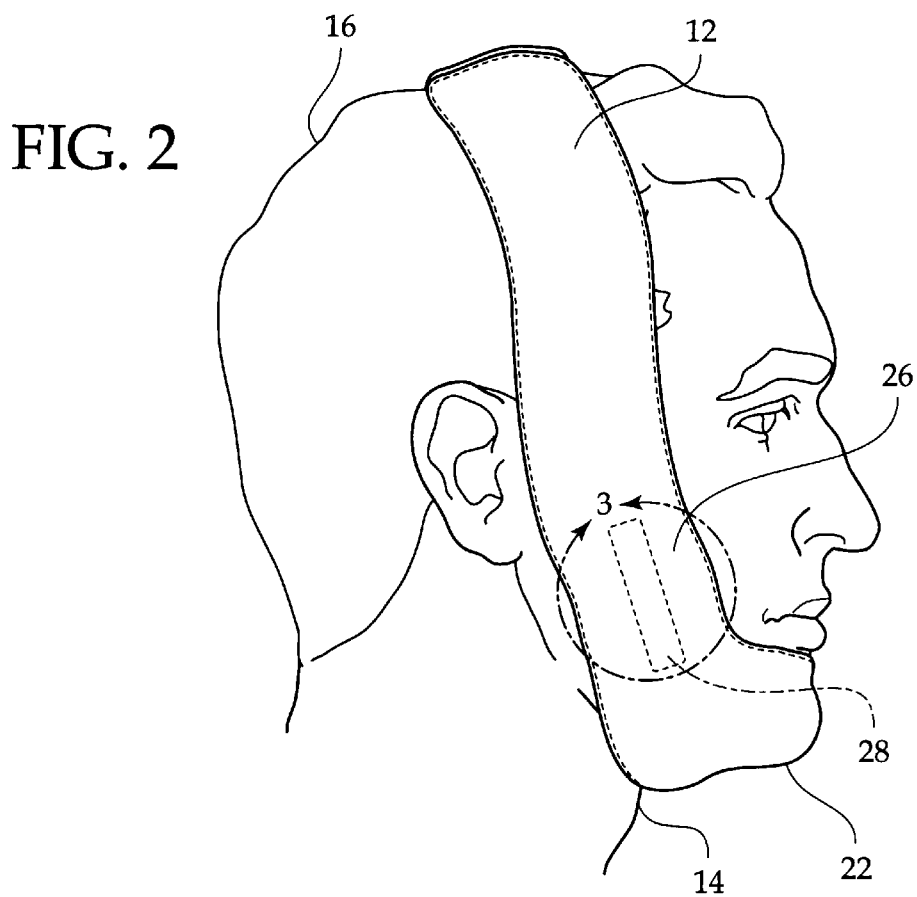
FIG. 2 is a side view of the present invention illustrated in use.
Figure 3:
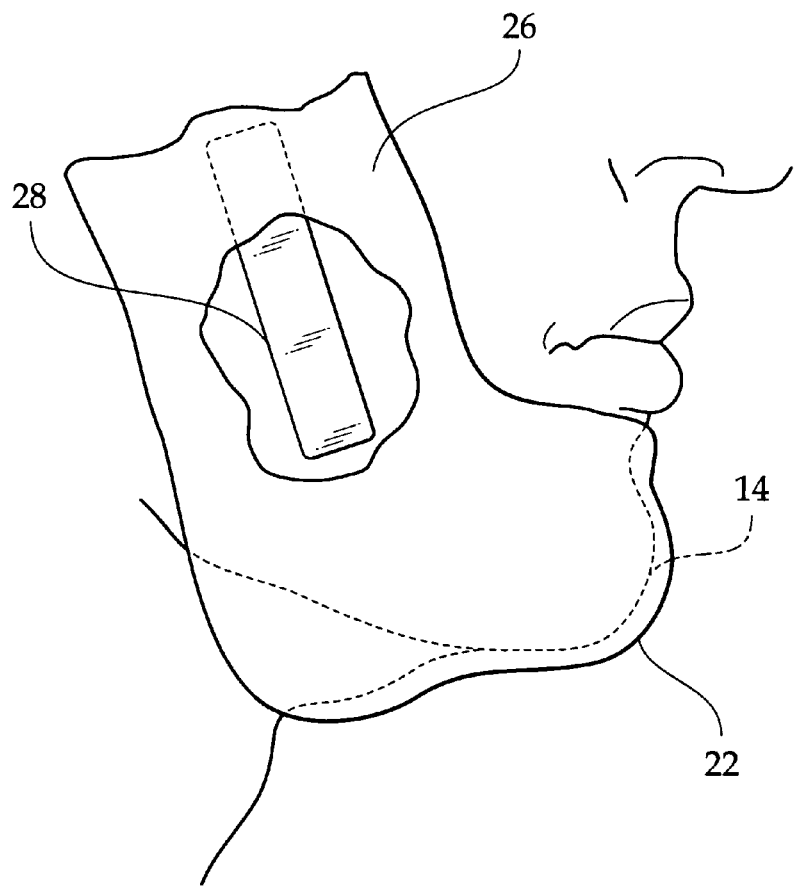
FIG. 3 is a sectional side view of the present invention illustrated in use.
Figure 4:
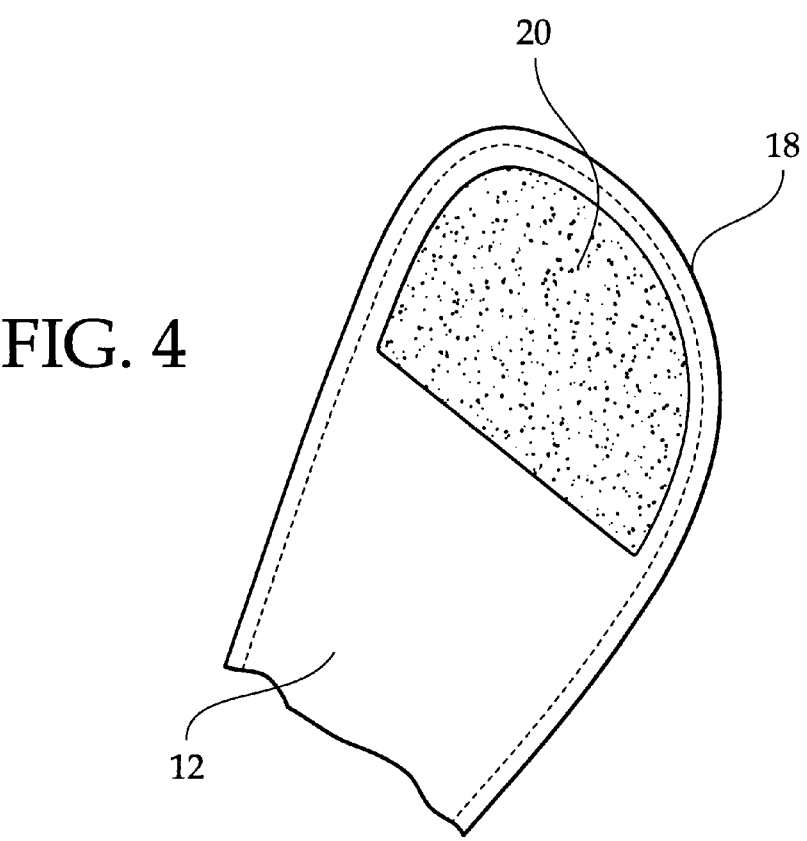
FIG. 4 is a sectional view of one of the free ends of the strap.

With reference now to the drawings, and in particular, to FIGS. 1 through 4 thereof, the preferred embodiment of the new and improved chin and face toning strap embodying the principles and concepts of the present invention and generally designated by the reference number 10 will be described.

Specifically, it will be noted in the various Figures that the device relates to a chin and face toning strap for exercising the muscles of the face while also stimulating the flow of blood to the face. In its broadest context, the device consists of an elongated strap portion and a pair of magnets. Such components are individually configured and correlated with respect to each other so as to attain the desired objective.

The elongated strap portion 12 is dimensioned for wrapping underneath a chin 14 and attaching atop a head 16 of a user. The elongated strap portion 12 is constructed of an elastic material. This allows the strap portion 12 to stretch and conform to the user's face while at the same time not limiting the movements of the mouth. The elongated strap portion 12 has opposed ends 18. The opposed ends 18 each have a hook and loop patch 20 disposed thereon. The hook and loop patches 20 couple together to secure the strap portion 12 under the chin 14 and to the head 16 of the user. The strap portion 12 has a chin portion 22 that is positionable under the chin 14 of the user. The chin portion 22 is defined by an enlarged section 24 dimensioned for receiving the chin 14 therein. The enlarged section 24 has padding disposed therein. The strap portion 12 has opposed cheek portions 26 positionable against cheeks of the user.

The pair of magnets 28 are secured within the cheek portions 26 of the elongated strap portion 12.

The present invention provides for the exercising of the chin muscles while also stimulating the flow of blood through the face to help retard the aging process. The strap portion 12, because of its elasticity, follows the contour of the face, under and around the chin 14 and extends up over both cheek areas to connect atop the head 14 via the hook and loop patches 20. The padding of the enlarged section 24 provides added comfort while wearing the device 10. The strap portion 12 will also provide tension when opening the mouth to further exercise the facial muscles. The magnets 28 will help stimulate the flow of blood through the face.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by Letters Patent of the United States is as follows:

1. A chin and face toning strap for exercising the muscles of the face while also stimulating the flow of blood to the face comprising, in combination:

an elongated one piece strap portion dimensioned for wrapping underneath a chin and attaching atop a head of a user, the elongated strap portion being constructed of an elastic material, the elongated strap portion having opposed ends, the opposed ends each having a hook and loop patch disposed thereon, the hook and loop patches coupling together to secure the strap portion under the chin and to the head of the user, the strap portion having a chin portion positionable under the chin of the user, the chin portion being defined by an enlarged section dimensioned for receiving the chin therein, the enlarged section having padding disposed therein, the strap portion having opposed cheek portions positionable against cheeks of the user;

a pair of magnets secured within the cheek portions of the elongated strap portion.

2. A chin and face toning strap for exercising the muscles of the face while also stimulating the flow of blood to the face comprising, in combination:

an elongated one piece strap portion dimensioned for wrapping underneath a chin and atop a head of a user, the elongated strap portion being constructed of an elastic material, the strap portion having a chin portion positionable under the chin of the user, the strap portion having opposed cheek portions positionable against cheeks of the user;

a pair of magnets secured within the cheek portions of the elongated strap portion.

3. The chin and face toning strap as set forth in claim 2 wherein the elongated strap portion has opposed ends, the opposed ends each having a hook and loop patch disposed thereon, the hook and loop patches coupling together to secure the strap portion under the chin and to the head of the user.

4. The chin and face toning strap as set forth in claim 2 wherein the chin portion is defined by an enlarged section dimensioned for receiving the chin therein.

5. The chin and face toning strap as set forth in claim 4 wherein the enlarged section has padding disposed therein.

* * * * *